United States Patent [19]

Kitney et al.

[11] Patent Number: 5,081,993

[45] Date of Patent: Jan. 21, 1992

[54] METHODS AND APPARATUS FOR THE EXAMINATION AND TREATMENT OF INTERNAL ORGANS

[75] Inventors: Richard I. Kitney, Fulham; Keith Straughan, Berkhamsted; Martin T. Rothman, London, all of United Kingdom

[73] Assignee: Circulation Research Limited, Boreham Wood, England

[21] Appl. No.: 488,007

[22] PCT Filed: Nov. 10, 1988

[86] PCT No.: PCT/GB88/00971

§ 371 Date: May 9, 1990

§ 102(e) Date: May 9, 1990

[87] PCT Pub. No.: WO89/04142

PCT Pub. Date: May 18, 1989

[30] Foreign Application Priority Data

Nov. 11, 1987 [GB] United Kingdom ............... 8726440

[51] Int. Cl.$^5$ ............................................. A61B 8/02
[52] U.S. Cl. ............................ 128/661.08; 128/916; 128/661.09; 128/662.06; 128/4
[58] Field of Search ................. 128/661.08, 661.09, 128/660.03, 916, 662.06, 4, 660.09, 24 A

[56] References Cited

U.S. PATENT DOCUMENTS

| | | | |
|---|---|---|---|
| 3,669,095 | 6/1972 | Kobayashi et al. | 128/659 |
| 3,779,234 | 12/1973 | Eggleton et al. | 128/660.10 |
| 3,817,089 | 6/1974 | Eggleton et al. | 128/660.10 |
| 3,938,502 | 2/1976 | Bom | 128/662.06 |
| 4,127,034 | 11/1978 | Lederman et al. | 73/626 |
| 4,140,107 | 2/1979 | Lancée et al. | 73/626 |
| 4,249,539 | 2/1981 | Vilkomerson et al. | 128/754 |
| 4,257,278 | 3/1981 | Papadofrangakis et al. | 73/861.25 |
| 4,271,706 | 6/1981 | Ledley | 73/614 |
| 4,319,580 | 3/1982 | Colley | 128/696 |
| 4,325,257 | 4/1982 | Kino et al. | 73/626 |
| 4,398,540 | 8/1983 | Takemura et al. | 128/660.05 |
| 4,576,177 | 3/1986 | Webster, Jr. | 128/303.1 |
| 4,589,419 | 5/1986 | Laughlin et al. | 128/660.03 |
| 4,608,986 | 9/1986 | Beranek et al. | 128/786 |
| 4,641,657 | 2/1987 | Ellis | 128/630 |
| 4,671,293 | 6/1987 | Shaulov | 128/661.01 |
| 4,672,963 | 6/1987 | Barken | 128/303.1 |
| 4,747,411 | 5/1988 | Ledley | 73/626 |
| 4,748,982 | 6/1988 | Horzewski et al. | 606/192 |
| 4,794,531 | 12/1988 | Morishita et al. | 364/414 |
| 4,821,731 | 4/1989 | Martinelli et al. | 128/662.06 |
| 4,887,605 | 12/1989 | Angelson et al. | 128/660.03 |

FOREIGN PATENT DOCUMENTS

| | | | |
|---|---|---|---|
| 083973 | 7/1983 | European Pat. Off. | 128/662.05 |
| 0123455 | 11/1984 | European Pat. Off. | 128/662.06 |
| 0173266 | 3/1986 | European Pat. Off. | 606/3 |
| 0234951 | 9/1987 | European Pat. Off. | 128/662.05 |
| 0253268 | 1/1988 | European Pat. Off. | 128/660.01 |
| 0260963 | 3/1988 | European Pat. Off. | 128/419 R |
| 0274129 | 7/1988 | European Pat. Off. | 606/7 |
| WO8100676 | 3/1981 | PCT Int'l Appl. | 604/20 |
| WO8502105 | 5/1985 | PCT Int'l Appl. | 128/660.04 |
| WO8504319 | 10/1985 | PCT Int'l Appl. | 128/661.01 |
| WO8802241 | 4/1988 | PCT Int'l Appl. | 128/661.01 |
| WO8904142 | 5/1989 | PCT Int'l Appl. | 128/662.05 |
| WO8904143 | 5/1989 | PCT Int'l Appl. | 128/662.05 |
| 809112 | 2/1959 | United Kingdom | 604/19 |
| 1160805 | 8/1969 | United Kingdom | 604/19 |
| 1176765 | 1/1970 | United Kingdom | 604/19 |
| 1210017 | 8/1970 | United Kingdom | 128/662.05 |
| 1402192 | 8/1975 | United Kingdom | 128/662.05 |
| 1415759 | 11/1975 | United Kingdom | 128/660.01 |
| 1427134 | 3/1976 | United Kingdom | 127/786 |
| 1445678 | 8/1976 | United Kingdom | 128/662.05 |
| 2015733 | 9/1979 | United Kingdom | 128/660.09 |
| 1590712 | 8/1981 | United Kingdom | 128/662.05 |
| 2027197 | 5/1983 | United Kingdom | 128/660.09 |
| 2108267 | 9/1983 | United Kingdom | 128/660.09 |
| 2057131 | 4/1984 | United Kingdom | 128/660.09 |
| 2073418 | 1/1985 | United Kingdom | 128/662.05 |
| 2091916 | 9/1985 | United Kingdom | 128/661.01 |
| 2173593 | 10/1986 | United Kingdom | 128/662.05 |
| 2157828 | 3/1987 | United Kingdom | 128/662.05 |
| 2156985 | 6/1987 | United Kingdom | 120/660.01 |
| 2197419 | 1/1991 | United Kingdom | 606/27 |

OTHER PUBLICATIONS

Binocular Stereoscopic Display for Echocardiography, Tanaka, IEEE, Feb. 1979.

Imaging Verterbral Artery, Wood, Ultrasound in Med. & Biol., vol. 6, Mar. 1980.

3-D Ultrasound Visualisation, Baxter, AFIPS, May 1980.

Ultrasound in Med. & Biol., vol. 6, pp. 329-339, "A Technique for Imaging the Vertebral Artery Using Pulsed Doppler Ultrasound," by C. P. L. Wood and H. B. Meire.

*Primary Examiner*—Francis Jaworski
*Assistant Examiner*—George Manuel
*Attorney, Agent, or Firm*—Richard M. Goldberg

[57] ABSTRACT

The internal examination of a human organ (3) is made by means of an ultrasonic probe (2) inserted into the organ (3), analogue echo signals from the probe being converted to digital signals (8) which are then stored in a digital computer (10) where they are manipulated to produce a variety of three-dimensional representations of the interior of the organ for display on a terminal (12) or as hard copy (13).

17 Claims, 12 Drawing Sheets

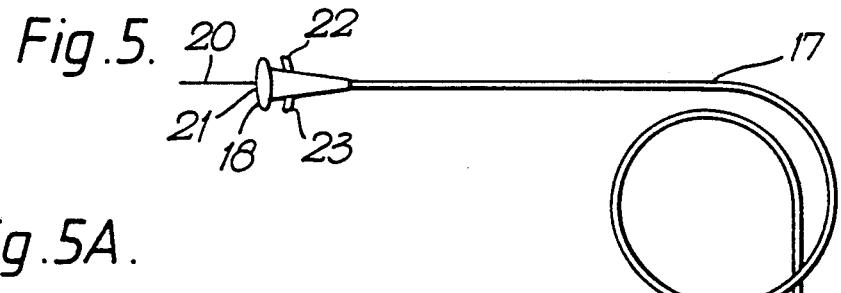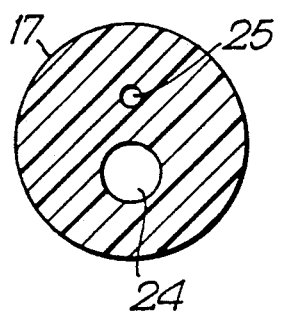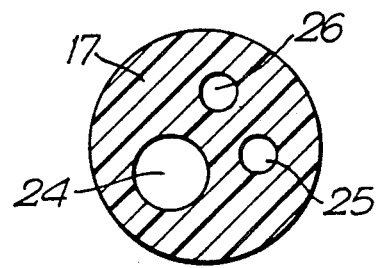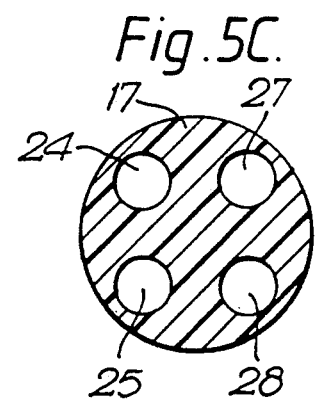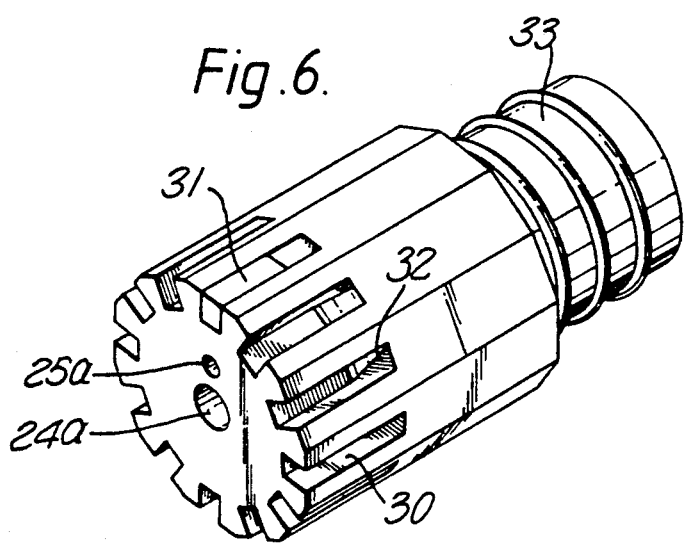

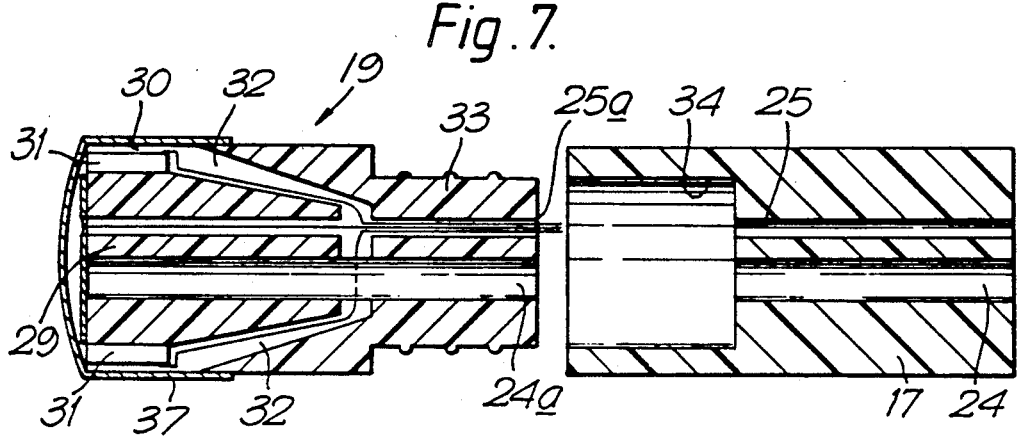
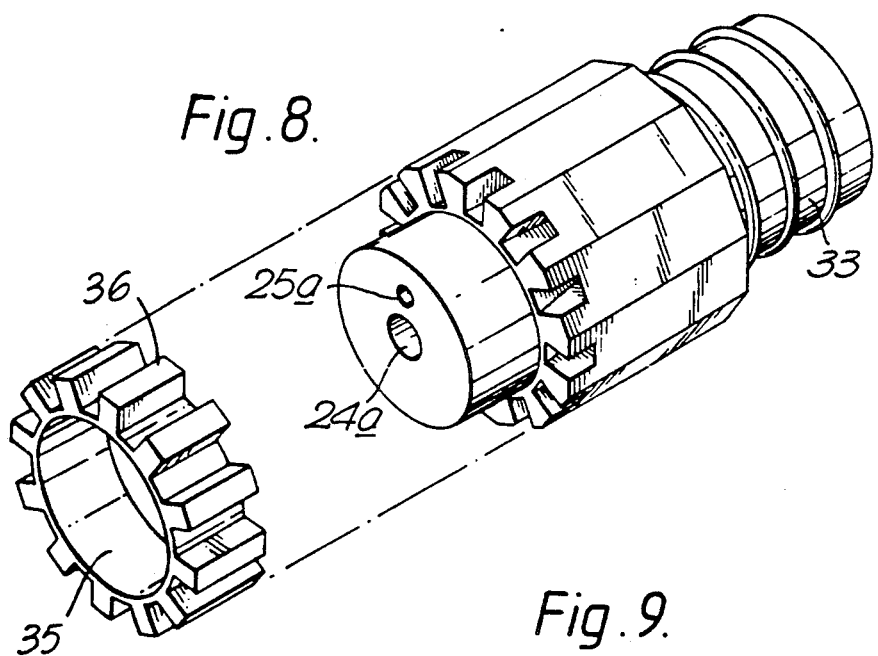
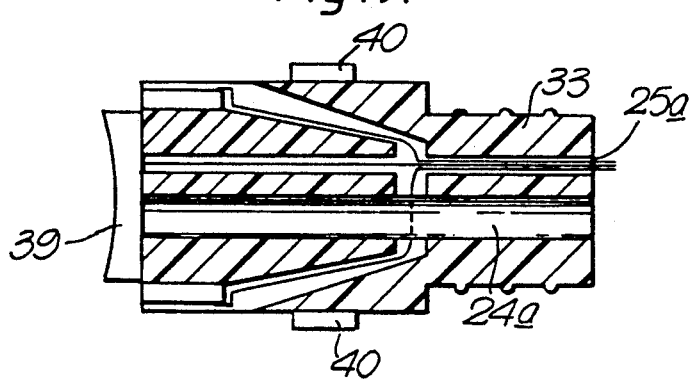

METHODS AND APPARATUS FOR THE EXAMINATION AND TREATMENT OF INTERNAL ORGANS

The present invention relates to methods and apparatus for the examination and treatment of internal organs of the human body.

It is already known to make an internal examination of an internal human organ, without recourse to surgery, by means of optically based equipment and also by means of equipment which makes use of the transmission and receipt of ultrasonic signals. The present invention is concerned with the latter approach and with providing a system and apparatus which will enable the shortcomings of existing equipment to be overcome thus providing the medical practitioner and hence the patient with the opportunity for a more accurate and timely diagnosis and hence treatment.

As indicated earlier it is known to use ultrasonic signals in order to create a visual representation of the interior of an internal human organ. In one known method a probe capable of emitting and receiving an ultrasonic signal is moved over the outside of the human body and a continuous two-dimensional visual representation of the internal cross-section of the human organ is generated from the ultrasonic signals reflected or attenuated by the organ. Whilst such equipment is easy to operate the visual representation of the interior of the organ is not very accurate and in any event is in only two dimensions.

The known prior art approaches to the problem of providing the medical practitioner with an accurate and useful visual representation of the interior of the human organ have concentrated on producing a real-time continuous two-dimensional image. This approach has inherent disadvantages which become particularly acute where it is desired to make an internal examination of an organ having a relatively small cross-section, in particular a human artery.

The present invention approaches this problem from the unexpected appreciation that a continuous real-time image is not necessary in order to enable the medical practitioner to obtain a clear internal picture of the organ.

According to the present invention a method for providing an image of the interior of a human organ or for visualising the flow of blood through it involves firing ultrasonic signals either from inside or outside the organ, detecting the echoes of those signals, digitising the echo signals, storing the digitised echo signals in a digital computer, manipulating the stored digitised echo signals in such a way as to provide an output from the computer which will give a three-dimensional visual representation of the interior of the organ which representation can be manipulated to enable the representation to be viewed from different aspects.

The signals obtained by the method of the present invention can also be used to provide so-called "tissue characterisation", that is information on the internal composition or make-up of tissue such as plaque which has formed on the inside of an artery. Such information would be of assistance to the medical practitioner in arriving at a diagnosis and a decision as to appropriate treatment.

The invention can be used to "characterise" live or dead tissue, i.e. it can also be used in connection with the field of pathology.

In the case of an artery, the ultrasonic signals would be fired from within the artery whereas it would also be possible for example to generate an image of the heart by means of ultrasonic signals fired from outside the heart but from within the human body itself.

According to the present invention, equipment for providing an image of the interior of a human organ comprises a combination of the following features:

a) a catheter for insertion into the human body;
b) an ultrasonic transducer assembly mounted on the catheter;
c) means for energising the transducer to generate ultrasonic signals;
d) means for receiving the resultant ultrasonic echo signals and converting them into digital signals;
e) a digital computer to which the digital signals are fed;
f) means for manipulating the digital signals when in the computer to enable a three-dimensional representation of the organ to be created and that representation to itself be manipulated to enable the respresentation to be viewed from different aspects and also to enable the structural make-up of tissue to be visually represented; and
g) means connected to the computer for visually displaying the three-dimensional representation.

According to the present invention a catheter for use with the method or equipment referred to earlier comprises:

a) a probe carried at one end of the catheter;
b) an ultrasonic transducer arrangement in the form of an annular assembly or transducer elements which encircle the probe at or near one of its ends; and
c) means to electrically connect the transducer elements to the other end of the catheter, which means either incorporates a multiplexing/demultiplexing circuit as such or comprises a wiring arrangement which has the effect of acting in a multiplexing or demultiplexing way, the purpose of either the circuit or the arrangement being to reduce the number of wires which run the length of the catheter.

How the invention may be carried out will now be described, by way of example only, and with reference to the accompanying drawings in which:

FIG. 5 shows a known construction of catheter for use in the system of FIG. 1;

Figure 1:
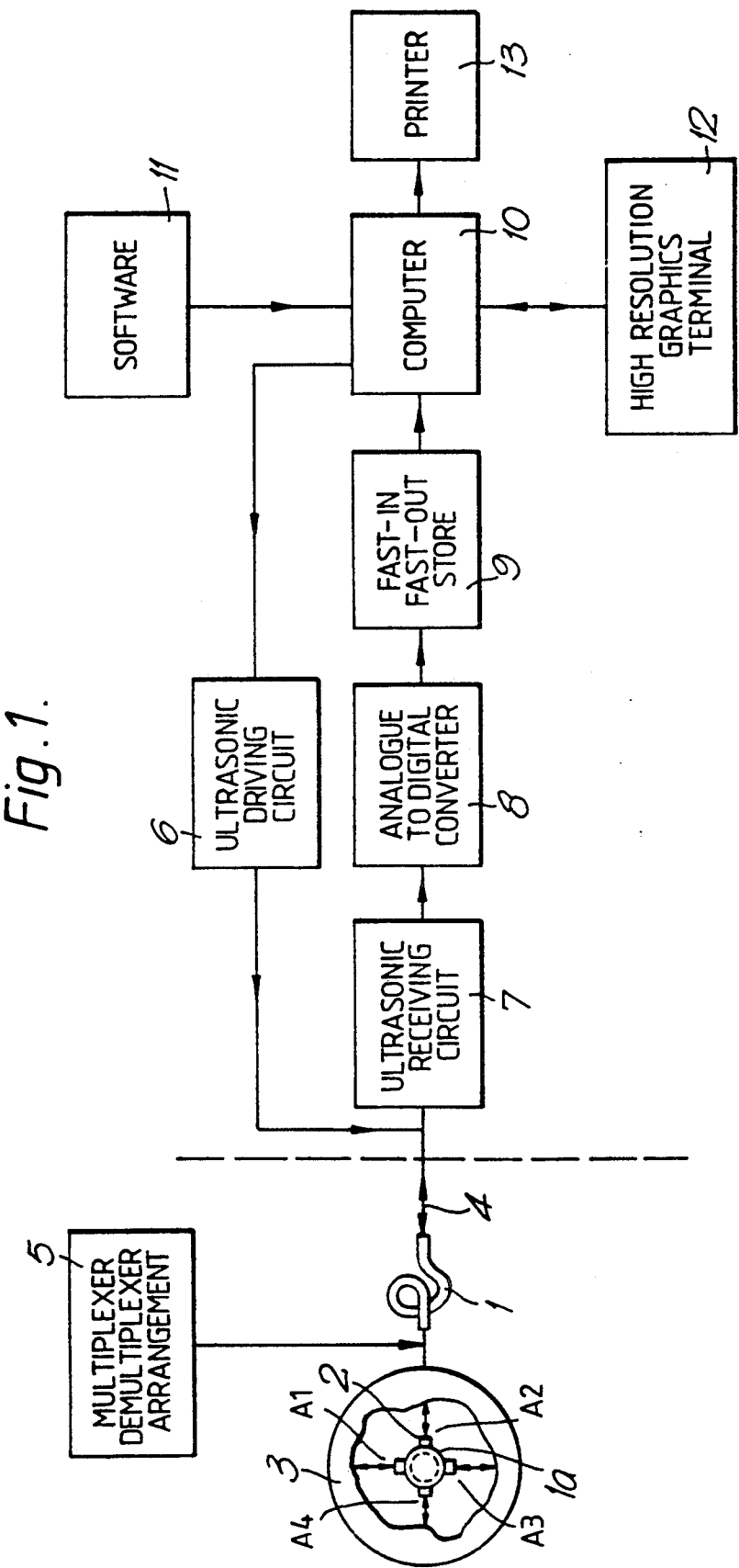
FIG. 1 is a block diagram of a system according to the present invention.
Figure 11:
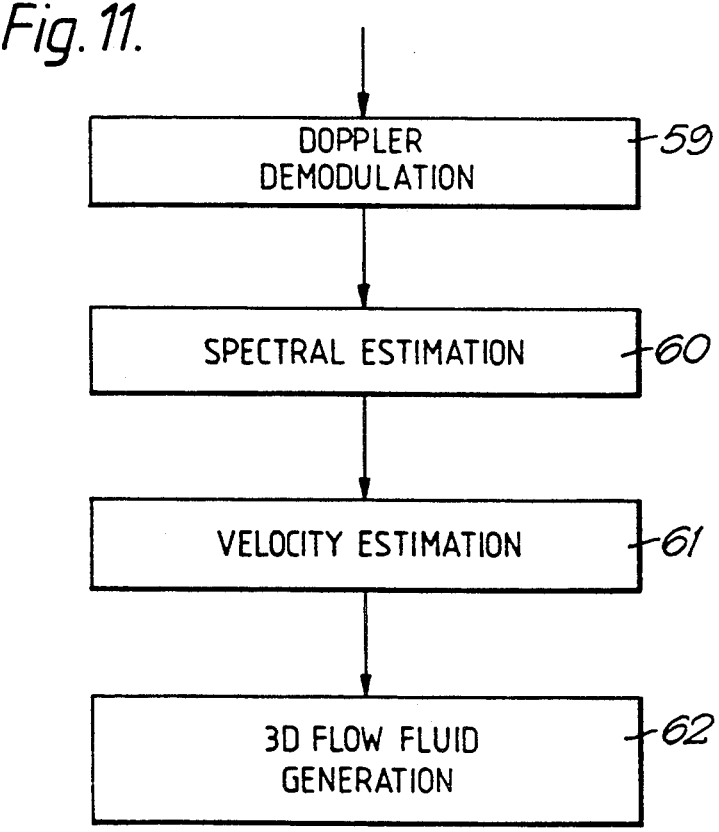
Figure 10:
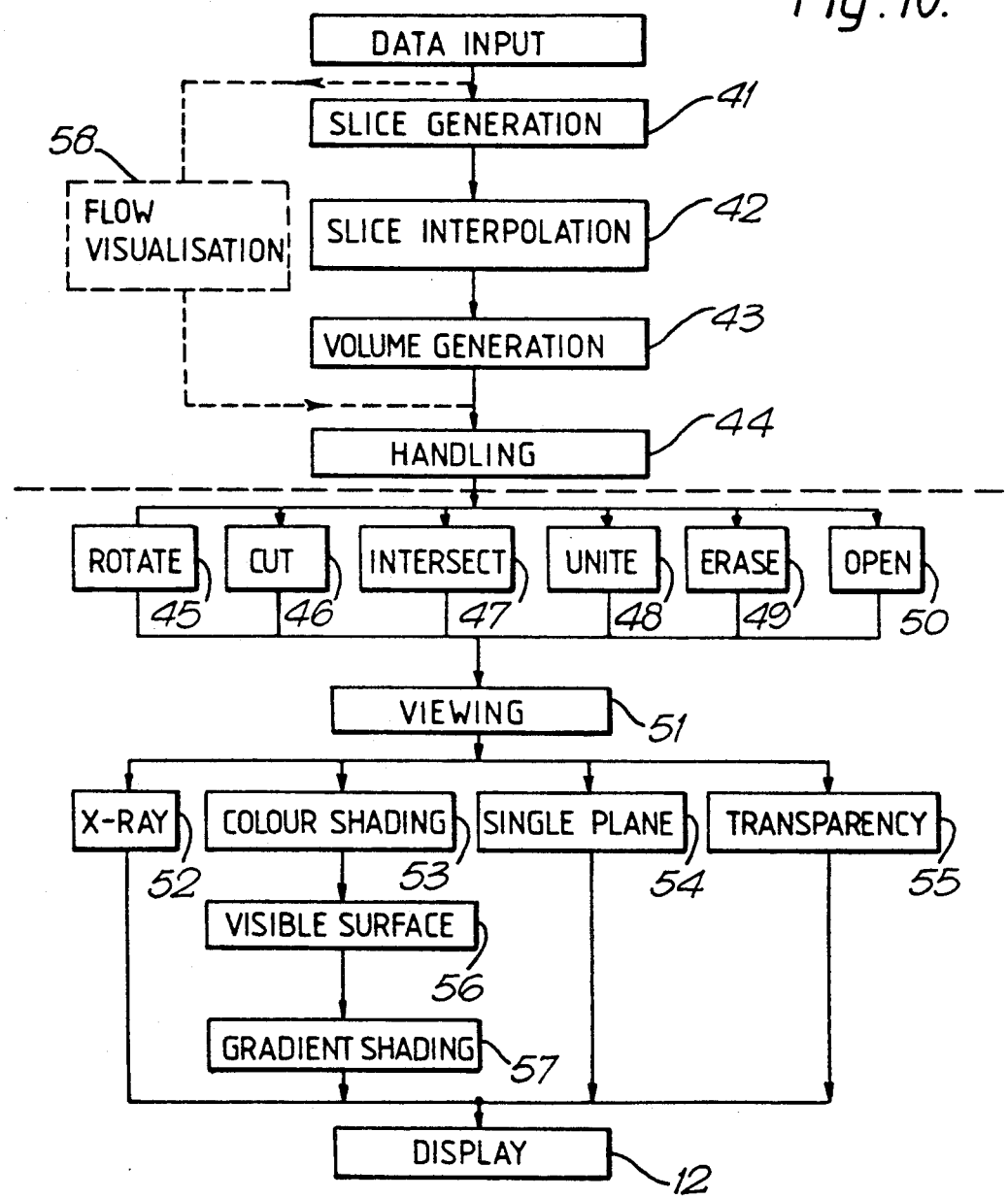

FIGS. 5A, 5B, and 5C are cross-sections illustrating different types of known catheter for different purposes;

FIG. 6 is a perspective view showing one form of the ultrasonic transducer assembly for mounting on the end of a catheter;

FIG. 7 is a longitudinal section taken on the line A—A of FIG. 6;

FIG. 8 is a view similar to FIG. 6 showing an alternative construction of ultrasonic transducer assembly;

FIG. 9 is a view similar to FIG. 7 illustrating a transducer assembly which is designed to provide treatment as well as diagnosis;

FIG. 10 is a flow diagram showing the logic of the software/programming used in the system of FIG. 1; and FIG. 11 is a flow diagram illustrating in more detail a modification or enhancement of the software illustrated in FIG. 10.

Figure 12:
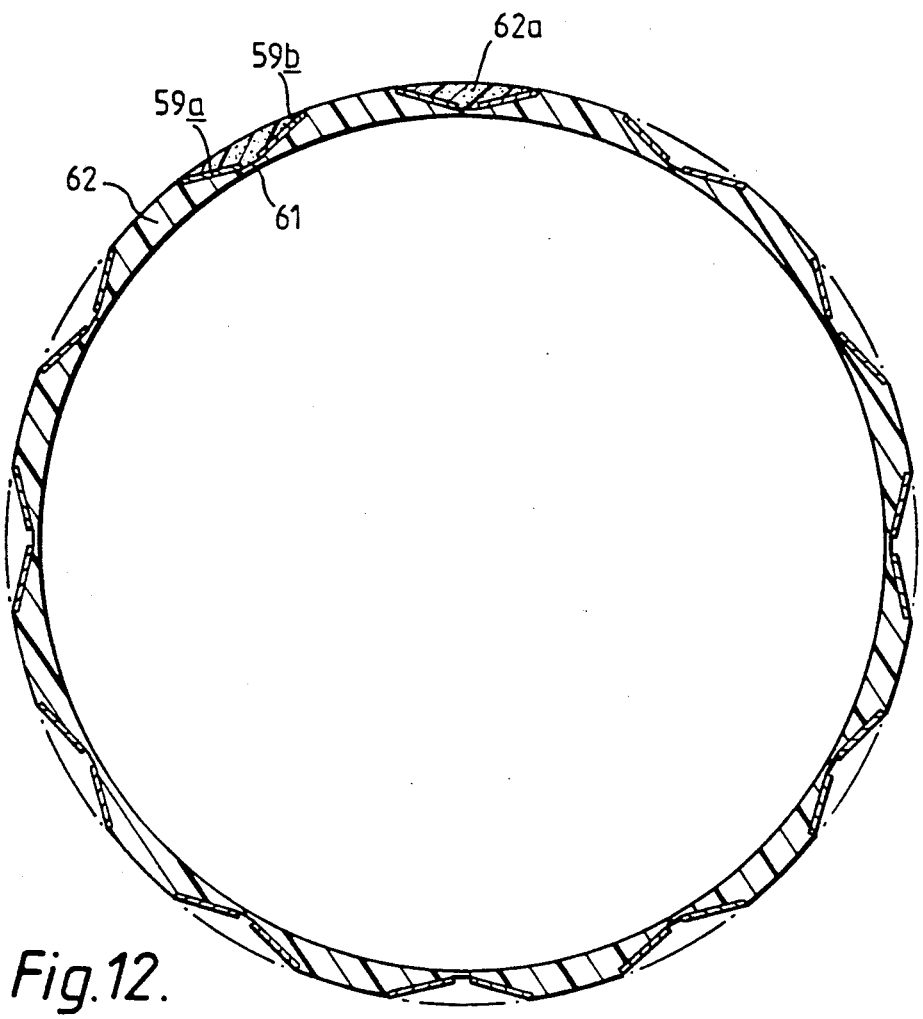
Figure 13:
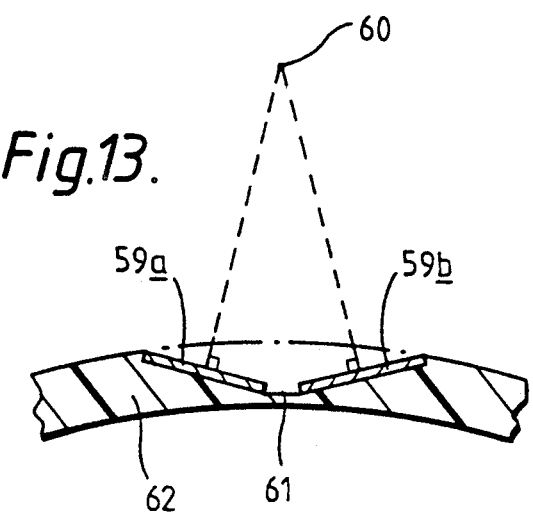
Figure 14:
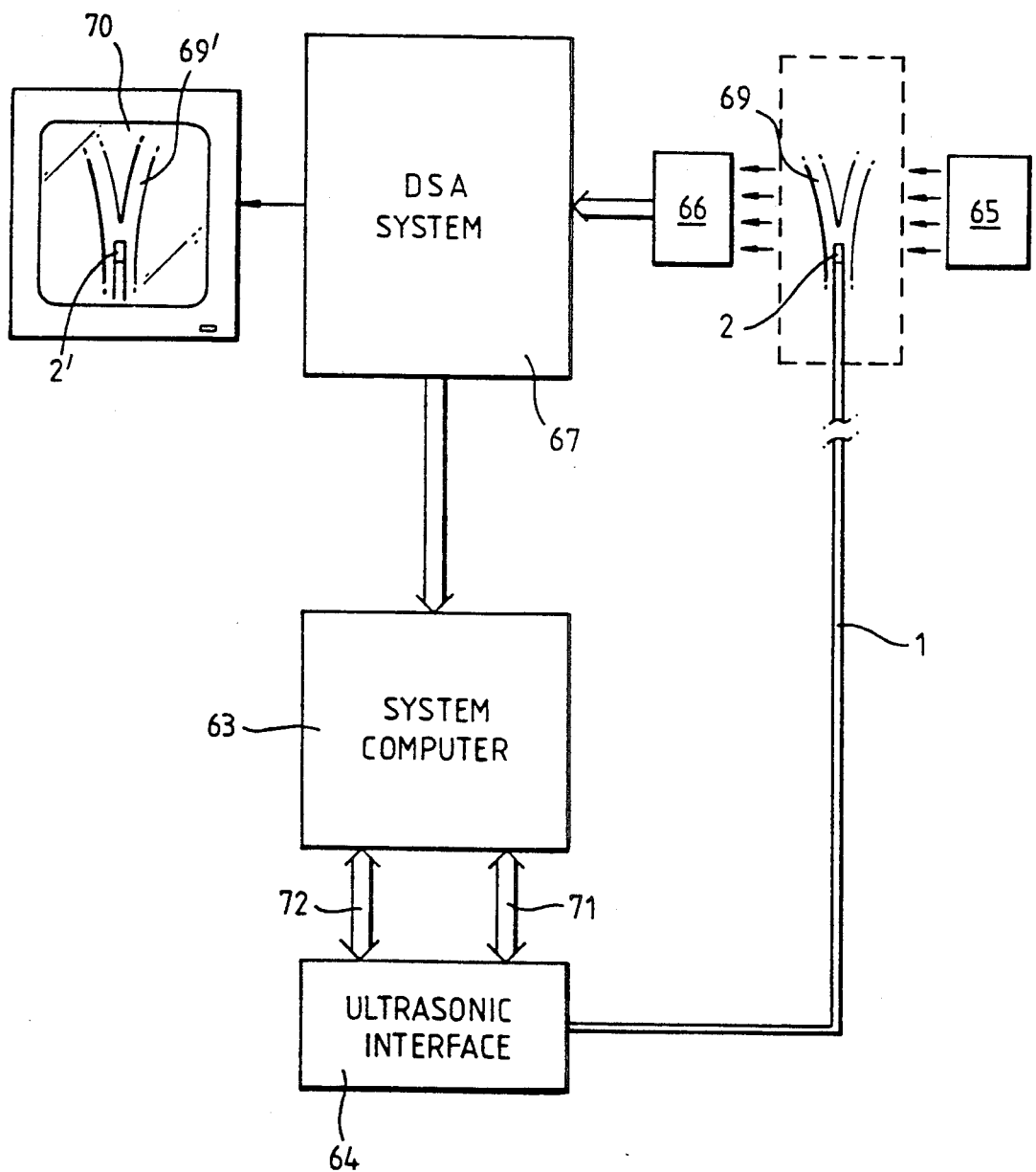
Figure 15:
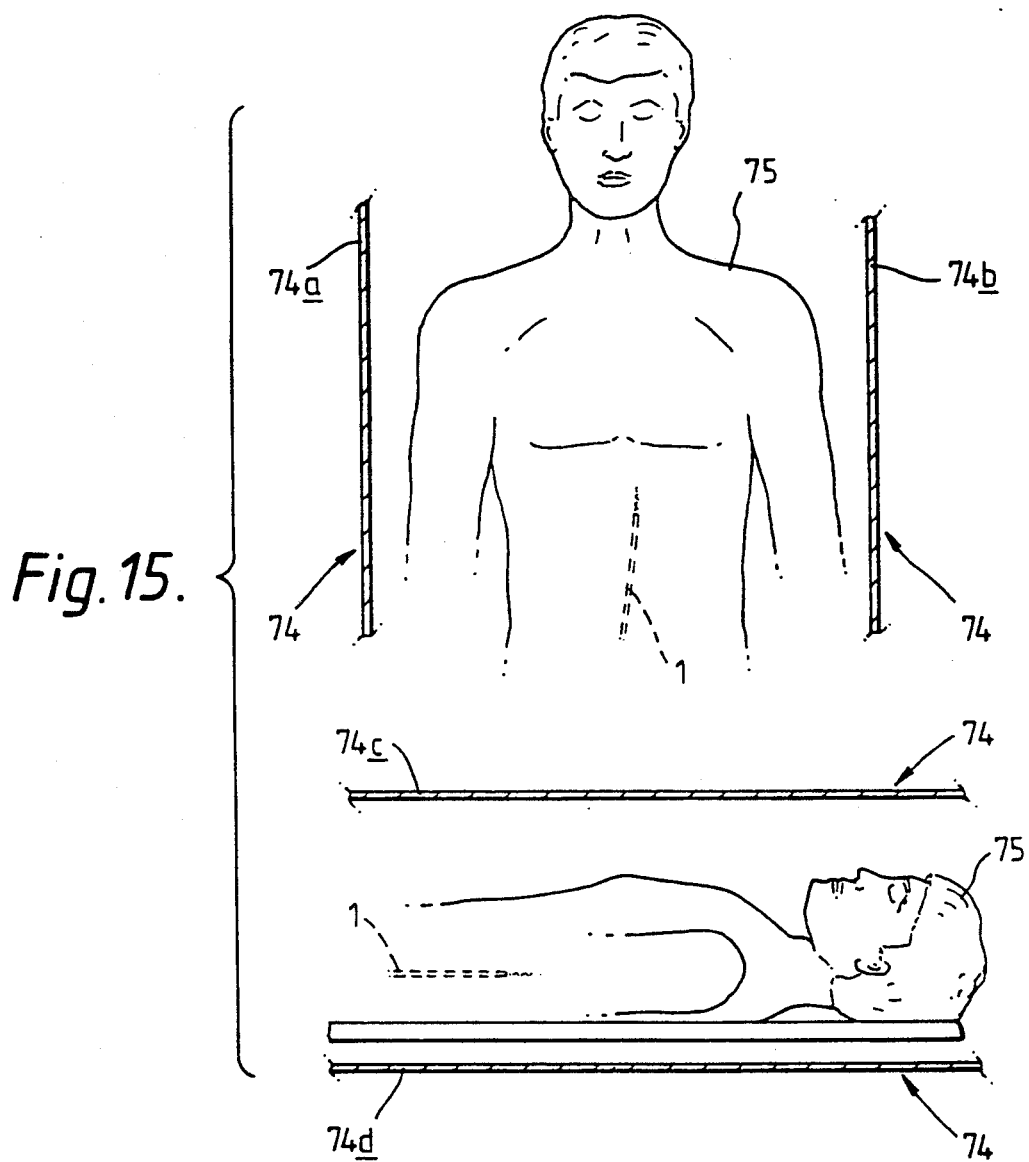
Figure 16:
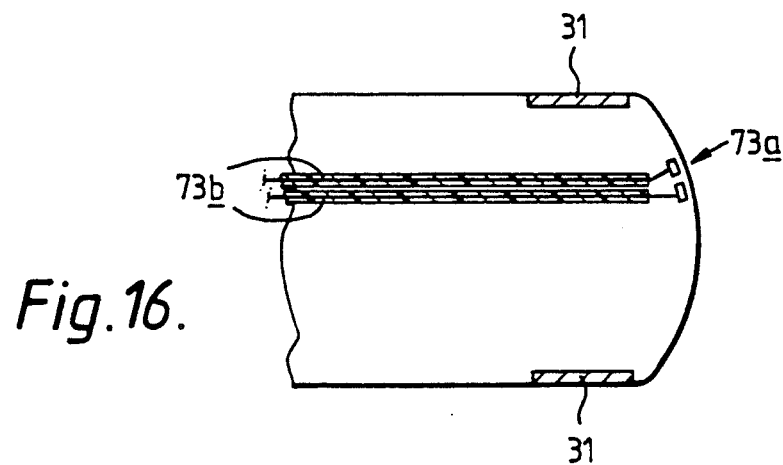
Figure 17:
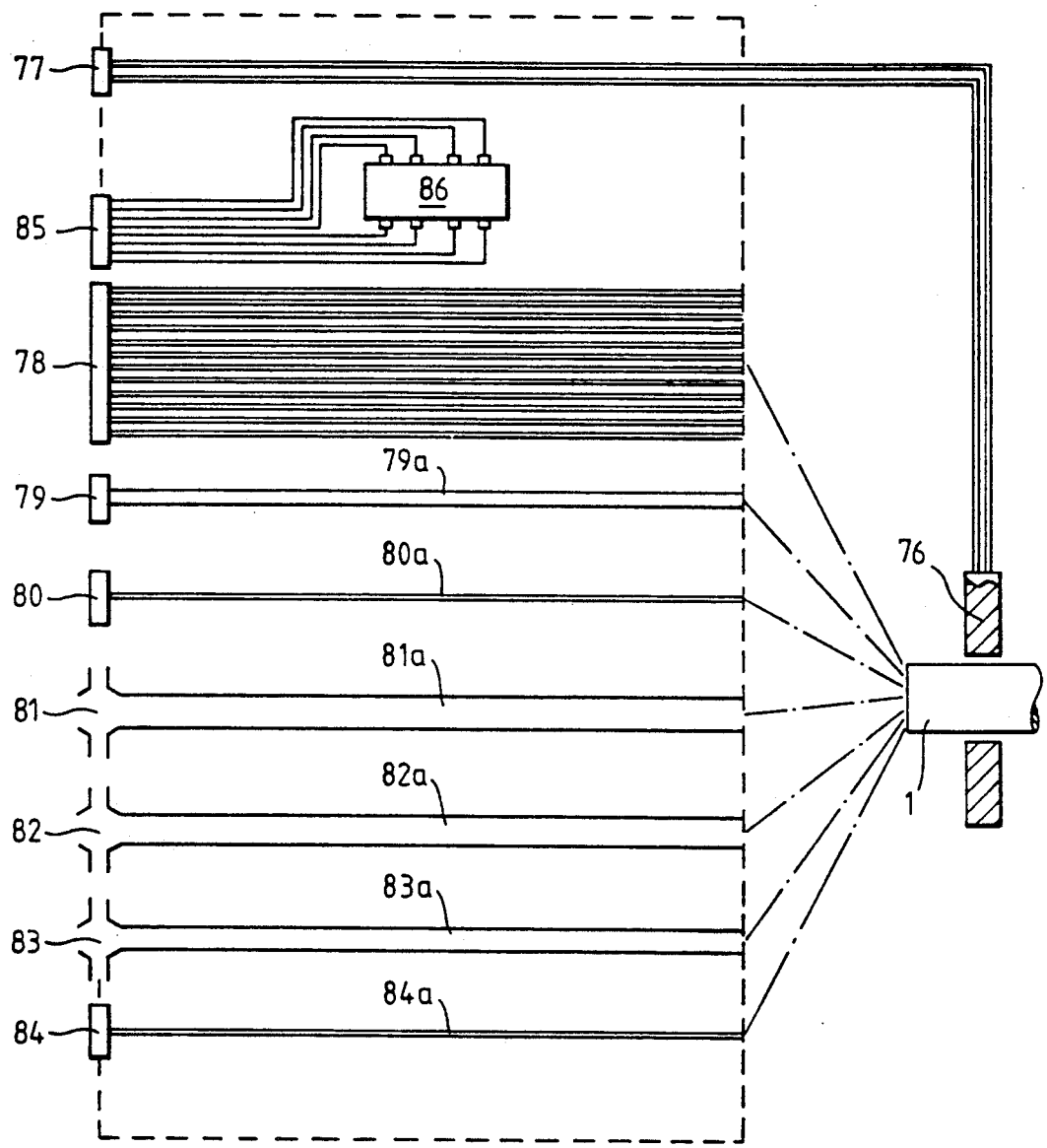
Figure 18:
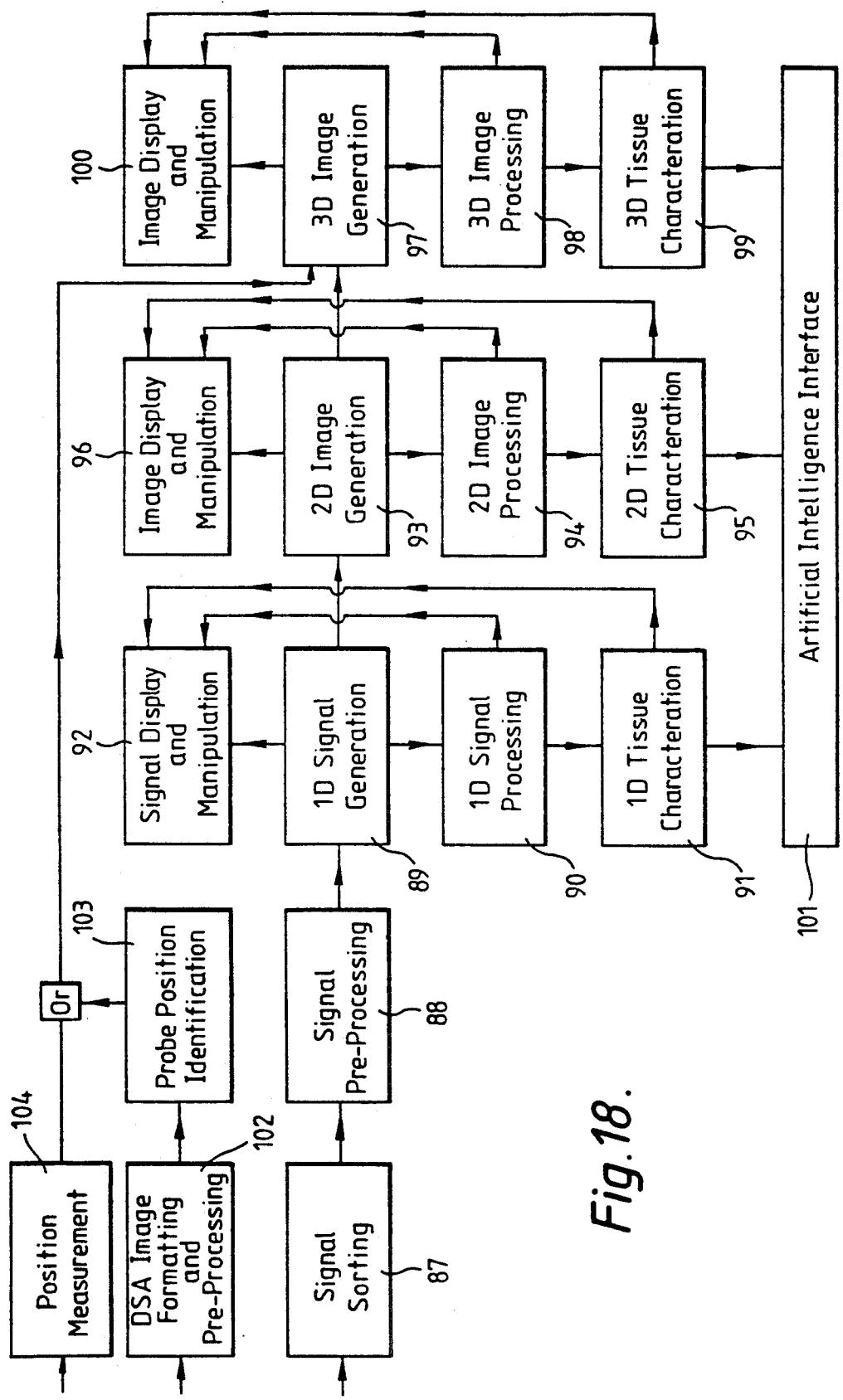

FIG. 12 is a diagrammatic cross sectional view of a further construction of ultrasonic transducer assembly;

FIG. 13 is a fragmentary enlarged view of part of the transducer assembly of FIG. 12;

FIG. 14 is a diagrammatic representation of a way of coupling the system of the present invention to a known X-ray system to indicate the position of the ultrasonic transducer assembly within the patient's body;

FIG. 15 is a diagrammatic representation of an alternative to FIG. 14 for indicating the position of the ultrasonic transducer assembly within the patient's body using a spark discharge;

FIG. 16 is an enlarged sectional view of the end of the probe shown in FIG. 15;

FIG. 17 is a schematic illustration of both the interface between the catheter and the echo signal processing system to the right of the broken line in FIG. 1 and also a further means for indicating the position of the probe within the patient's body using a micrometer; and FIG. 18 is a block diagram showing in more detail that part of the system shown at 10, 11 and 12 in FIG. 1.

FIG. 1

FIG. 1 is a block diagrammatic representation of a method for providing an image of the interior of a human organ particularly an artery.

A catheter 1 for insertion into a human artery 3 has a free end 1a on which is mounted an annular ultrasonic transducer assembly 2, the other end of the catheter being electrically connected by connection 4 to the equipment shown to the right of the broken line in FIG. 1.

The electrical connection 4 is described in detail in connection with FIGS. 3 and 4 but in effect includes a wiring arrangement which acts as a multiplexer/demultiplexer 5 which functions to reduce the number of wires which would otherwise need to pass through the catheter 1 in order to connect the transducer assembly 2 to the equipment illustrated diagrammatically to the right of the broken line in FIG. 1.

The transducer assembly 2 is energised by a driving circuit 6 to cause the transducer assembly 2 to emit ultrasonic signals. The transducer assembly 2 responds to echoes of the emitted signals and this causes the generation of echo signals which pass back through the multiplexer/demultiplexer arrangement 5 to an ultrasonic receiving circuit 7 and then to an analogue-to-digital converter 8 which translates the analogue electrical echo signals into digital signals.

These digital echo signals are then fed to a fast-in-fast-out data store 9 from whence they are fed into a digital computer 10.

The digital computer 10 is programmed by means of software 11 in such a way that the digital echo signals are transformed into signals which when fed to a high resolution graphics display terminal 12 will enable a three-dimensional representation of the interior of the artery 3 to be displayed.

The software 11 enables the data to be manipulated so that the three-dimensional representation can be viewed from different aspects.

A hard copy of the three-dimensional representation can be obtained by means of a printer 13.

Figure 3A:
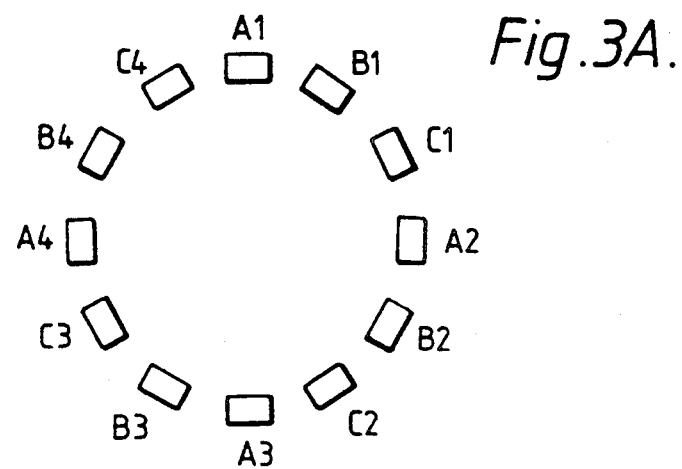
FIGS. 3A and 3B are diagrammatic representations of a single annulus transducer arrangement and its associated electrical wiring.
Figure 3B:
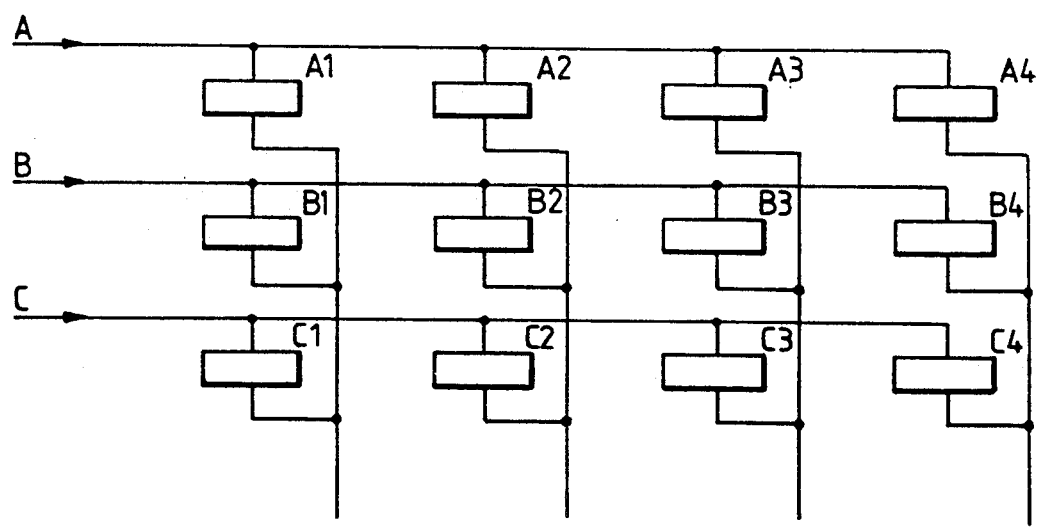
Figure 4:
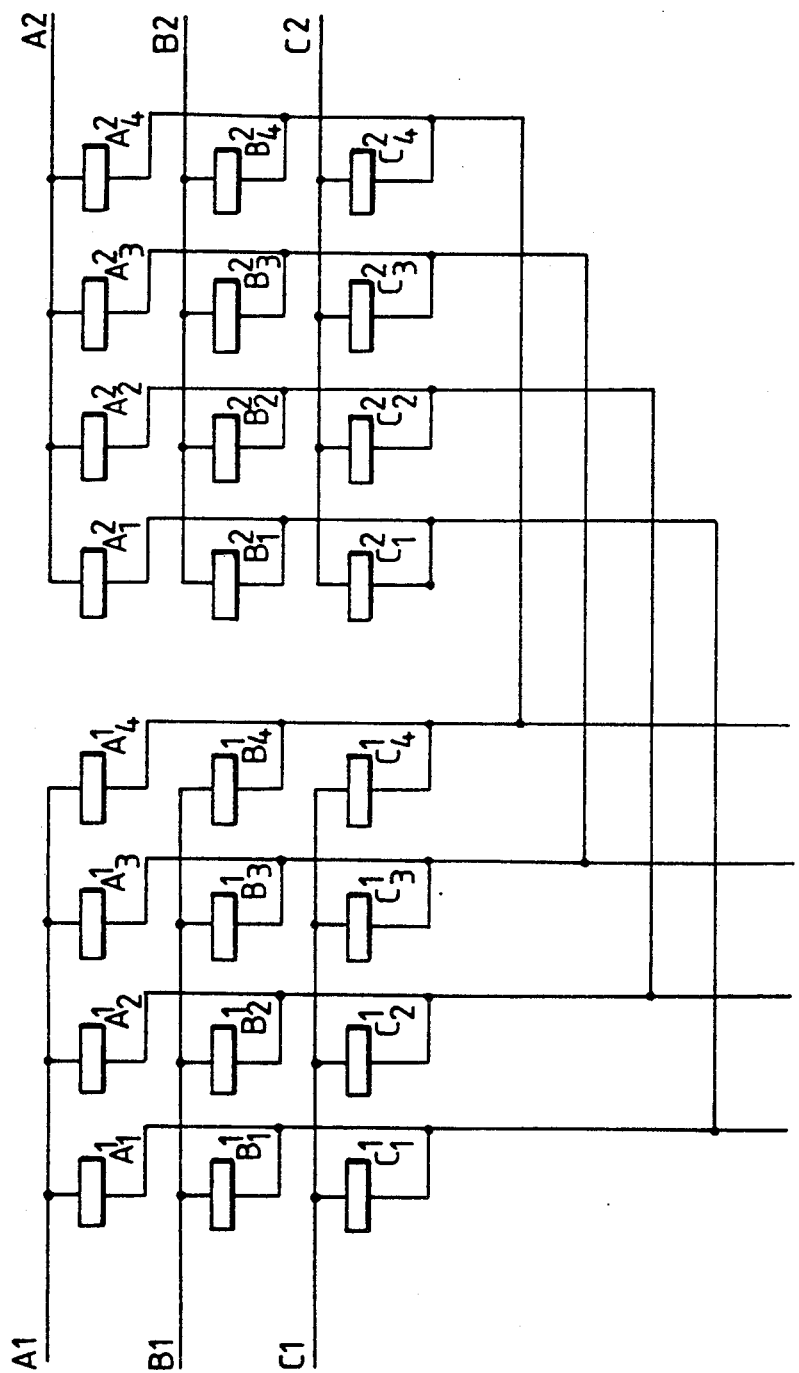
FIG. 4 is a view similar to FIG. 3B showing the wiring of a transducer arrangement having two annuli.

The multiplexer/demultiplexer arrangement 5 could consist of a multiplexer/demultiplexer circuit as such or could comprise a logic wiring arrangement two examples of which are shown in FIGS. 3 and 4 later. If a multiplexer/demultiplexer circuit as such were used it could be constructed from a standard analogue switch array such as the Siliconix types SD5400, SD5401 or SD5402 DMOS FET Quad.

The ultrasonic driving circuit 6 and receiving circuit 7 could be of the kind disclosed by Donald W Baker in his paper entitled "Pulsed Ultrasound Doppler Blood Flow Sensing", IEEE Transactions on Sonics and Ultrasonics Vol. SU17 No. 3 1970.

The analogue to digital converter 8 could be of the type disclosed in Datel Corporation's Application Note DTL-18.

The fast-in-fast-out store 9 could be of the kind disclosed by J E Pedersen in his article entitled "Fast Dedicated Microprocessor for Real Time Frequency Analysis of Ultrasound Blood Velocity Measurements" : Medical and Biological Engineering and Computing Vol. 20 pages 681-686.

The digital computer 10 would be of any suitable kind and capacity such as a DEC Micro Vax-11 having eight megabytes of RAM, 70 megabytes of hard disk and a 90 megabyte tape streamer. The connection between the digital computer 10 and the high resolution colour graphics terminal 12 is made via a 16-bit parallel interface.

The high resolution colour graphics terminal 12 is fitted with 8 planes, has a maximum spacial resolution of 1448 (X) by 1024 (Y) at a depth resolution of 8 bits (256 colours). If required the depth resolution can be increased up to as many as 24 bits, although in detriment to the spacial resolution. All the programmes used in the software 11 in use assume 256 colours and 1448×1024 pixels. Examples of terminals which meet these requirements are the Sigmex 6200 series, and certain types of Tektronix and Ramtech terminals.

In order to give an overall appreciation of how the method illustrated in FIG. 1 operates there will now follow a brief description although aspects of the method will then be described in more detail in relation to the remaining figures in the drawings.

The geometry and construction of the probe carrying the annular transducer assembly 2 is selected and designed to be compatible with the nature and flow of the fluid within the artery 3 and with the internal diameter of that artery. Each piezo-electric element of the transducer assembly is connected once per scan for less than 100 µS through the multiplexer/demultiplexer arrangement 5 to the ultrasonic driving and receiving circuits 6 and 7 respectively. A 1 µS burst of high frequency signal from the driving circuit 6 pulses the selected piezo-electric crystal. The resulting ultrasonic pressure wave produced by the crystal is emitted radially to insonate the internal wall of the artery 3. Echoes from this interface, and other acoustic impedance discontinuities in the sound path, are received by the same piezo-electric crystal element. The pulse-echo signal after amplification by the receiving circuit 7 is combined with a "start-of-scan" pulse and with a switching circuit pulse. This composite radio frequency signal is then digitised by a "flash" analogue to digital converter 8, i.e. a converter which can handle high frequency signals. The resultant 8 bit samples are then stored simultaneously in a high speed random-access-memory.

When a complete scan by all the elements of the transducer assembly have been stored, the data is downloaded through a parallel data link to the digital computer 10. The digital computer 10 runs sophisticated signal processing and reconstruction software 11 to create a high resolution image of the artery cross-section, or other aspect, on a high resolution colour graphics display terminal. The frequency of energisation of the transducer elements would preferably lie in the range 1 to 20 MHz the axial length of each of the transducer elements is preferably between 2 mm and 8 mm. The best results have been obtained with a length of 8 mm.

FIG. 2

This illustrates the ultrasonic signals fired by the transducer elements and their associated echo signals. Specifically the ultrasonic signals are indicated at 14a to 14j inclusive and the associated echo signals at 15a to 15j inclusive, synchronising pulses being indicated at 16a to 16i inclusive.

FIGS. 3 AND 4

Figure 2:
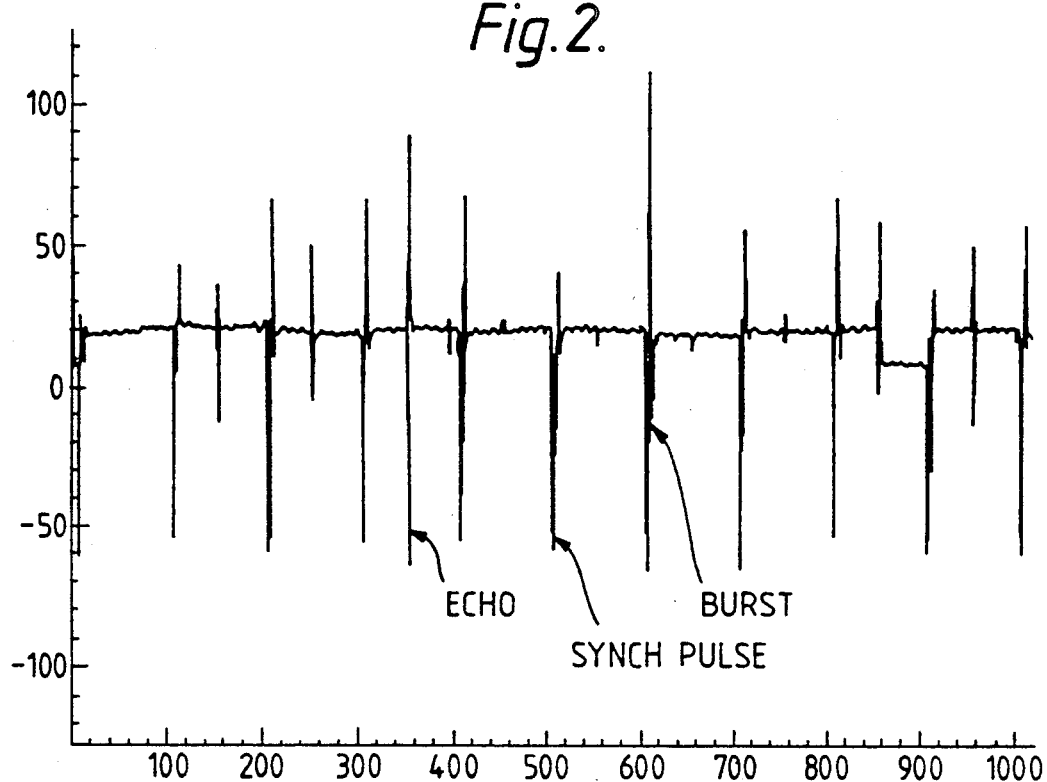
FIG. 2 illustrates the timing of the "burst" and "echo" signals of FIG. 1.

As mentioned in connection with FIG. 1 the transducer assembly 2 comprises a number of transducer elements each of which consists of a piezo-electric crystal preferably made of lead zirconium titanate (PZT). In FIG. 1 four such elements are illustrated and FIG. 2 is based on the assumption that there are ten transducer elements. The number of elements can vary but the higher the number the greater the resolution or clarity of the image that will be produced.

FIGS. 3 and 4 illustrate in more detail two specific arrangements of transducer elements and the way in which they are connected electrically in order to reduce the number of wires which have to pass along the tubular catheter 4, i.e. the wiring arrangements illustrated act in effect as a multiplexer/demultiplexer.

In FIG. 3 the transducer arrangement consists of twelve transducer elements labelled A1, B1, C1, A2, B2, C2, A3, B3, C3, A4, B4, C4 taken in a clockwise direction. The elements A1, A2, A3, A4 are electrically connected in parallel so that they are energised at the same time (see also FIG. 1). The four elements B1, B2, B3, B4 are similarly connected to be energised together as are the elements C1, C2, C3, and C4, as illustrated.

In operation four elements are energised at a time in the order A1, A2, A3, A4 together, then B1, B2, B3, B4 together, then C1, C2, C3, C4 together, and so on. With the wiring arrangement shown in FIG. 38 although there are twelve transducer elements there are only four wires leading through the tubular catheter to energise them. This wiring arrangement thus acts as the equivalent of a multiplexer/demultiplexer circuit.

In FIG. 4 the transducer arrangement consists of two side-by-side annuli each of twelve transducer elements, as compared with FIG. 3 in which there is only a single annulus of twelve elements. The wiring arrangement of each of the two annuli is similar to that of FIG. 3 but the elements of the two annuli are interconnected so that on each firing pulse four elements from each annulus are energised together, i.e. eight elements are energised at a time.

The sequence of energising the transducer elements is as follows. The group A1 elements in the first ring are energised together with the group B2 elements in the second ring. The group B1 elements in the first ring are energised with the group C2 elements in the second ring. The group C1 elements in the first ring are energised with the group A2 elements in the second ring.

It will be noted that immediately adjacent elements in the two rings are not energised together e.g. A1 with A2. The reason for this is to reduce the likelihood of cross-talk between the two rings.

More than two rings could be used in which case non-adjacent rings could have equivalent transducer elements fired together because the risk of crosstalk would already have been reduced by the spacing apart of these two rings by an intermediate ring or rings.

FIG. 5

This illustrates a typical known type of catheter which consists of a plastic tube 17 which has a handle 18 at one end and a tip member 19 at the other. A guide wire 20 can be passed through the tube 17. The handle 18 is provided with an axially located aperture 21 through which the guide wire 20 can pass. The handle is also provided with further radially located apertures 22 and 23.

FIGS. 5A, 5B and 5C illustrate some known cross-sections for the catheter tube 17, these cross-sections being designed for different medical applications of the catheter.

In the cross-section of FIG. 5A the tube 17 has a lumen or passage 24 to accommodate the guide wire 20 and a second lumen or passage 25 to accommodate micro-coaxial wiring.

In the cross-section of FIG. 5B the tube 17 has lumens 24 and 25 as in FIG. 5A but also has a third lumen 26 through which compressed air or other appropriate gas can be passed to inflate a balloon built into the end of the catheter tube 17 at or near its tip 19. Such a construction of catheter is well known.

In the cross-section of FIG. 5C there are lumens 24 and 25 as before but also two further lumens 27 and 28. Lumen 27 is intended to accommodate a fibre-optic channel for the application of laser angioplasty in known manner. The lumen 28 is intended to accommodate a pressure sensor (not shown) in known matter.

FIGS. 6-8

The catheter(s) shown generally in FIGS. 5, 5A, 5B and 5C are of known construction. A catheter according to the present invention is characterised by the construction of the tip 19 or probe. FIGS. 6-8 illustrate examples of the tip 19 or probe according to the present invention.

In FIGS. 6 and 7 the tip 19 of the present invention is made of a plastic material such as polyvinylchloride (p.v.c.) and has a core section 29 through which lumens 24a and 25a pass. The core section 29 has twelve grooves 30 formed around its circumference, each groove being adapted to accommodate a single piezo-electric crystal transducer element 31.

Each groove 30 is connected to the lumen 25a by a passage 32. A micro-coaxial cable extends from the aperture 22 in the handle 18, through the catheter tube 17 and its constituent strands terminate at the transducer elements 31.

The tip 19 has a spigot portion 33 which is shaped and dimensioned to be a friction fit in a cup-shaped end 34 to the catheter tube 17. The tip 19 can thus be designed with the appropriate number and location of lumens to match up with the known types of catheter tube 17. In practice because each catheter tube is used only once, and also because of the requirement to provide a medically safe construction, the junction between the spigot 33 and the inner surface of the cup shaped end 34 would be sealed by epoxy resin. Furthermore, the passages 32 would also be filled with epoxy resin.

In FIGS. 6 and 7 (and FIGS. 3 and 4) the approach for obtaining the required degree of resolution is to increase the number of transducer elements, e.g. by having one or more rings each of twelve transducer elements. Scanning of the organ is achieved by in effect electronically rotating a four-pole transducer element in relation to each ring.

An alternative approach involves the physical rotation of the transducer elements to achieve the same objective. In this approach the transducer elements would be mounted on a member which itself is rotatably mounted on the core section 29 of the probe. Some suitable drive means would be provided for rotating the member. The drive means could comprise a wire which passes back through the catheter tube 17 to itself be rotated by a suitable electric motor, for example. The connection between the wire and the member could take various forms.

The advantage of having a rotatable transducer arrangement is that the same image resolution can be achieved with fewer transducer elements compared with FIGS. 3, 4, 6 and 7 or a higher resolution can be achieved for a given number of transducer elements. The degree of resolution will depend on the number of transducer elements carried by the rotatable member and the speed of rotation of that member, generally the higher the speed the higher the resolution.

FIG. 8 is a view similar to FIG. 6 but showing an alternative form of the transducer arrangement. In this alternative form the transducer arrangement consists of a single ring or annulus 35 of piezo-electric crystal which has grooves 36 which extend parallel to the axis of the tip 19 and adjacent pairs of which define the transducer elements A, B, C etc (FIGS. 3 and 4). A smooth tubular sheath 37 of ultrasonically transparent material covers the transducer assembly in order to facilitate the insertion and movement of the catheter through the artery.

FIG. 9

This is a view similar to FIG. 7 but in this embodiment the probe or tip at the end of the catheter is provided with a further piezo-electric transducer arrangement, the purpose of which is to break up or disintegrate plaque which has formed on the inside of the artery.

This additional transducer arrangement is designed to emit relatively low-frequency ultrasonic signals which will have the effect of causing the plaque to resonate and thus disintegrate.

This additions transducer arrangement can take a number of forms, two alternatives of which are shown in FIG. 9.

The first alternative consists of a single transducer element 39 mounted on the end face of the core section 29, the transducer element 39 having a concave surface 39a so that it will focus the ultrasonic emitted signals at a substantially axial point in relation to the core member 29.

The alternative further transducer arrangement consists of a number of transducer elements 40 mounted around the outside surface of the core member 29 so that they emit ultrasonic signals in a substantially radially outward direction in relation to the axis of the artery.

FIG. 10

This illustrates the logic of the software which is shown schematically at 11 in FIG. 1.

As indicated earlier the data received from the transducer assembly is in the form of "snap-shots" as each of the sets of four transducer elements is fired and the associated echo signals received. These signals and associated echoes in effect give the instantaneous radial distance of points of the inside of the artery and points through the thickness of the arterial wall from the transducer elements that have been fired. This step is shown at 41 in FIG. 10 and labelled "SLICE GENERATION", each firing and associated echoes representing a "slice" through the artery. However, because this "slice" is produced by a finite number of transducer elements it does not give a complete picture of the cross-section of the artery but only an approximation to that cross-section. It is therefore necessary to interpolate between the points on the cross-section that have been ascertained by the signals fired from and received by the individual transducer elements and to interpolate between adjacent "slices". This interpolation step is indicated at 42 in FIG. 10 and labelled "SLICE INTERPOLATIQN".

Interpolation between adjacent "slices" can be achieved, for example, by known so-called spatial correlation techniques. This involves comparing the spacial features of individual "slices" using similar mathematics to those used for cross-correlation functions employed in time series analysis.

The software of the present invention digitises each "slice" and stores the image information of each "slice" in terms of the basic picture elements or pixels. The three-dimensional model is then constructed from the digitised "slices" which are of course in the correct sequence, the three-dimensional model being made up of so-called "voxels" (three-dimensional "pixels") thus allowing the details of irregular anatomical lesions to be accurately modelled. This is in contrast with known commercially available software for three-dimensional solid modelling which is based on the concept of modelling an object using simple geometric shapes called "primitives" which are in effect taken from a library of pre-determined shapes. Further information on this known approach can be found in "Principles of Interactive Computer Graphics" by Foley and Van Dam, published by Prentice-Hall in 1982.

The advantages of the approach adopted by the present invention (i.e. using "voxels") is that it is then possible to rapidly manipulate the representation and take sections through it etc because the orientation of each individual "voxel" making up the total representation or model is not critical since each one is so small in relation to the total representation. This contrasts with the known method using "primitives" where the sizes of the latter are significant in relation to the total representation and consequently their orientations are critical to the obtaining of an accurate representation or model and therefore each "primitive" would have to be individually re-oriented during each manipulation of the representation or model.

The next step is to in effect integrate the various interpolated slices of the artery in order to produce a representation of the artery in three dimensions, this step being referred to as "VOLUME GENERATION" and indicated at 43 in FIG. 10.

After this has been done the data representing the three-dimensional image of the artery can be handled or manipulated in a number of ways in order to provide different aspects of that three-dimensional image. This step is indicated in FIG. 10 by box number 44 labelled "HANDLING".

In FIG. 10 the steps illustrated below the broken line are all concerned with the different manipulations that can be carried out on the three-dimensional representation that has already been produced by means of the steps above the dotted line. More specifically the steps labelled "ROTATE", "CUT", "INTERSECT", "UNITE", "ERASE" and "OPEN" are all concerned with manipulating the three-dimensional representation in a particular way. Specifically "ROTATE" refers to rotating the three-dimensional representation so that it can be viewed from different angles. The manipulation "CUT" refers to in effect removing a segment of the three-dimensional representation so that the interior can be viewed at that particular point. The manipulation "INTERSECT" refers to taking two three-dimensional representations and combining them for example in order to provide a visual representation of a Y-shaped artery. The manipulation referred to as "ERASE" is concerned with removing part of the three-dimensional representation and the manipulation referred to as "OPEN" is concerned with in effect notionally cutting the artery in a longitudinal direction and opening it up flat so that the interior of the artery can be seen in terms of contours.

An important advantage of the present invention lies in its power and flexibility to slice the solid three-dimensional representation or model (contained in three-dimensional "voxel" space) in any orientation. Hence any of a number of two-dimensional slices can be reproduced and further image processing of each slice undertaken to, for example, enhance certain features of the tissue.

It should be emphasised that the various manipulations just described are only examples of those which could be carried out.

The remainder of FIG. 10 illustrates the different ways in which the three-dimensional representations can actually be displayed. For example the representation can be presented in the form of a simulated X-ray picture i.e. with the background darker than the foreground. This is represented at 52 in FIG. 10. The boxes marked 53, 56 and 57 in FIG. 10 indicate different ways in which the image can be coloured. The box 55 labelled "TRANSPARENCY" refers to the possibility of presenting an image which has a uniform tone.

The software is written in a high level language, e.g. FORTRAN 77 running under VMS 4.4., and has a large range of features some of which have already been described with reference to FIG. 10.

The software has been written in a form which is entirely menu driven and control of the system would preferably be effected via a "mouse" with the rotation of the images being controlled by analogue controls.

Furthermore the computer 10 could be provided with an array processor in order to speed up the processing of the data, thus enabling the user to rotate a three-dimensional model image in real time, although the image itself has, as indicated earlier, been generated in non-real-time.

The software interface between the FORTRAN programmes and the terminal 12 consists of a series of routines for controlling the terminal. In the case of a Sigmex terminal these routines form a library called WKS77 which is like the system known as GKS (Graphical Kernel System).

FIG. 11

In FIG. 10 the processing diagrammatically illustrated below the dotted line can be used to manipulate and display any image produced by the steps indicated above the dotted line. In FIG. 10 the steps above the dotted line are concerned with generating data representative of a three-dimensional item such as an artery but the software below the dotted line can be used to manipulate data which is representative of other things.

More specifically the probe already described could be used to generate signals which are indicative of the blood flow within an artery and this data could be processed and manipulated to give a visual representation of that blood flow. This possibility is shown diagrammatically by the box marked "FLOW VISUALISATION" at 58 in FIG. 10.

It is already known to use ultrasonic signals for the assessment of arterial disease by estimating the velocity of blood flow in an artery. These known systems make use of the Doppler principle.

In the prior art approach pulses of ultrasonic signals cause multiple reflections from red blood cells flowing in the artery. In these systems only a small spacial section of the flow is analysed, this being referred to as the "sample volume" and is obtained by range gating the reflected ultrasonic signals. Further information on this prior art approach can be found in a paper entitled "Pulsed Ultrasound Doppler Blood Flow Sensing" by Donald W Baker in the IEEE Transactions on Sonics and Ultrasonics Vol.. SU17 No. 3 1970. In the present invention there will be multiple software range gates so that flow information along an entire radial path will be stored and hence the basic data required to calculate the entire two dimensional flow field will be obtained from the complete array of transducers. Flow profiles in any plane can then be calculated using the system software already described.

FIG. 11 illustrates diagrammatically the steps involved in the "FLOW VISUALISATION" indicated at 58 in FIG. 10.

Further background information relevant to data processing methods referred to above and to the "flow visualisation" method are:

KITNEY, R I, TALHAMI, H and GIDDENS, D P, (1986). "The Analysis of Bloody Velocity Measurement by Auto Regressive Modelling". Journal Theoretical Biology 120, pages 419–442.

KITNEY, R I, GIDDENS, D P, (1986) "Linear Estimation of Bloody Flow Wave Forms Measured by Doppler Ultrasound" In Med Info 86. Ed R Salamon, B, Blum and M Jorgensen. Published by North Holland Vol. 2 pages 672–678.

KU, D N and GIDDENS, D P, (1983) "Pulsatile Flow in a Model Carotid Bifurcation Anterio Sclerosis" —Vol. 3 pages 31–39.

FIGS. 12 & 13 1 7

In situations where the present invention is to be used to visualise the interior of organs having a significantly greater internal dimension than an artery it is possible to construct the probe with a much greater external diameter. For example the invention can be used to produce transoesophagal, trans-vaginal, trans-urethral and trans-rectal imaging. As a result it is possible to increase the number of annuli of transducer elements in the transducer assembly, for example five annuli. Also each annulus could accommodate a larger number of transducer elements. By this means an increase in resolution is achieved. Furthermore, an arrangement of transducer elements as shown in FIGS. 12 and 13 could be employed which could enable so-called tissue characterisation data to be obtained.

In this arrangement of transducer elements two crystals 59a and 59b of a pair are inclined towards one another so that ultrasonic signals emanating from them focus at a common point 60 radially outwardly from the position of the crystals. Each crystal of a pair operates at a different ultrasonic frequency from the other crystal of the pair. This can be achieved by variations in the crystal thickness. The probe wall is indicated at 62.

For clinical purposes the gap 61 between adjacent crystals of a pair together with the indentation formed between them would preferably be filled by a material which is transparent to ultrasonic frequencies, for example an epoxy resin 62a. The purpose of this is to produce a smooth surface to facilitate the passage of the transducer arrangement through the body of the patient.

The crystals would be energised and the echo signals transmitted back by means of micro-coaxial cables of the kind referred to in connection with FIGS. 7 and 9.

The purpose and advantage of the arrangement of FIGS. 12 and 13 is that tissue characteristic data can be obtained as a result of the differential ultrasonic back-scatter which results from the use of two frequencies. The same effect could be achieved by using a single dual-frequency crystal in place of the pairs of crystals 59a and 59b shown in FIGS. 12 and 13.

FIG. 14

The system of the present invention as previously described will give the medical practitioner a picture of the internal organ as the catheter passes through it. However, this will be a very localised picture and will not provide the medical practitioner with an overall view as to exactly where the probe at the end of the catheter is located within the arterial system of the patient's body.

FIG. 14 illustrates in diagrammatic form an arrangement whereby the system of the present invention, already described, is combined with a known X-ray system to in effect superimpose the image provided by the present invention on the overall X-ray image provided by the known system. By this means the medical practitioner is provided with a very convenient means for gaining an accurate overall picture.

The linking of the two systems could also enable tissue characterisation to be obtained.

FIG. 14 illustrates diagrammatically one way in which the two systems could be integrated.

The system of the present invention as shown to the right of the broken line in FIG. 1 is generally indicated at 63 and 64 in FIG. 14 the catheter and probe being indicated by 1 and 2 respectively within an artery 69 of the patient.

A known X-ray source is indicated at 65 and a known X-ray transducer at 66. The computer 63 connects the system of the present invention to the known X-ray system 67 in such a way that the output from the X-ray system 67 is a combined image 70 which includes the X-ray image $69^1$ and an image $2^1$ of the probe 2 within the arterial system of the patient.

The known X-ray system 67 is referred to as an X-RAY digital subtraction angiography or DSA IMAGING SYSTEM in the art.

The system described with reference to FIG. 14 operates in accordance with the internationally accepted ACR NEMA (American College of Radiology, National Equipment Manufacturers Association) standard for imaging systems and can therefore readily import images from any other system which is formatted under the ACR NEMA protocols. Thus a simple interface (preferably parallel though not necessarily so) between the system computer of the present invention and that of the DSA system (typically a VAX) will permit DSA images to be imported and displayed on the system of the present invention together with the ultrasound images generated by the latter system.

The controlling of the firing of the elements in the transducer assembly is effected via the computer data bus 71. The resultant echo signals are fed via the data bus 72.

In order to render the probe easily visible to the X-ray system a characteristic pattern of X-ray opaque dots (for example made of gold) are provided on the tip of the catheter to allow its precise position to be automatically located within the DSA image. In order to effect this automatic location known template matching or other pattern recognition procedures could be used. If a so-called "bi-plane" DSA system is used i.e. one in which two DSA images are provided at right angles, then the precise location of the catheter can be determined in three dimensions. This information can be used to build a full three-dimensional image from the composite scans of the system and also for the automatic co-relation of the ultrasound and DSA image data for visualisation and/or tissue characterisation.

A further advantage of this arrangement is that it permits the easy X-ray detection of the catheter tip should it become detached from the body of the catheter during its use.

FIGS. 15 and 16

These Figures illustrate an alternative method to that shown in FIG. 14 for identifying the position of the catheter 1 within the body of the patient. In this alternative method the catheter 1 is provided with a spark generating arrangement 73 so that when energised the resulting spark will be detected by means of an electrode array 74 which consists of four plates 74a, 74b, 74c and 74d. The strength of signal generated by the plates in response to the spark will be a function of the distance of the spark from the particular plate. In this way the sum of the signals of the four plates will enable the position of the probe to be determined. The patient's body is diagrammatically illustrated at 75.

FIG. 17

This figure illustrates three further aspects of the present invention namely:

(i) another method of giving an approximate indication of the position of the probe within the patient:
(ii) the interface between the catheter and the echo signal processing system of the invention: and
(iii) automatic catheter identification.

A system has already been described in connection with FIG. 14, whereby the position of the probe within the arterial system of the patient can be visualised. FIG. 17 illustrates diagrammatically a system which enables an approximate and less accurate assessment of the position of the probe within the patient to be made based entirely on measuring the distance that the probe has been inserted into the body of the patient.

Essentially this arrangement involves the use of an electronic micrometer and stepping motor assembly 76 which, in operation, moves the catheter into the patient and generates an electrical signal indicative of the distance the catheter has been inserted. The electronic micrometer could be used without the motor because instead of the latter the catheter could be inserted manually.

The signals from the electronic micrometer 76 are fed via an interface 77 to the system computer (63 in FIG. 14).

As well as the interface 77, for this optional feature of the invention, FIG. 17 illustrates other interfaces between the catheter and the electronic signal processing system shown to the right of the broken line in FIG. 1.

The main and essential interface is shown at 78 between the microcoaxial cables in the catheter and the system.

Other interfaces for the optional features described with reference to FIGS. 5A, 5B and 5C are shown at 79 to 82.

Specifically interface 79 relates to the fibre-optic channel in lumen 27 in FIG. 5C for the application of laser angioplasty the fibre optic cable being represented at 79a; interface 80 relates to the pressure sensor in lumen 28 (FIG. 5C) the connecting microcoaxial cable being shown at 80a; interface 81 relates to the guide wire 20 in lumen 24 of FIG. 5A the channel for the wire being shown at 81a; and interface 82 relates to the angioplasty balloon lumen 26 of FIG. 5B the channel for the balloon being shown at 82a.

Interface 83 is concerned with the insertion of a fluid, such as a saline solution into the catheter and/or a dye in order to create contrast in the X-ray picture the associated channel being indicated at 83a.

Interface 84 is concerned with the measuring of blood flow using the Doppler principle already described with reference to 58 in FIG. 10, the connecting coaxial cable being shown at 84a.

The third aspect of the invention illustrated in FIG. 17 relates to a means for automatically identifying the type of catheter being used and thereby automatically setting up the appropriate parameters in the system so that the correct signals are sent to the probe on the catheter and the resulting echoes are processed in the appropriate manner.

In order to achieve this, the end of the catheter which is adapted to be connected to the system (known in the art as the "proximal" end or interface) is provided with some means which is characteristic of that catheter and which can be "interrogated" by the system. In other words the catheter has characteristics which render it "intelligent". This can be achieved in a number of ways but preferably by incorporating a ROM (read-only-memory) integrated circuit 86 in the proximal end of the catheter. This ROM would have built into it all the necessary characteristics of the particular catheter so that when connected to the system it can be interrogated by it.

The characteristics which could be built into the ROM could include the following;
(i) a manufacturer's code so that the system can recognise which catheters are acceptable for use with it;
(ii) a serial number which is logged by the system to prevent a catheter from being reused;
(iii) an application code intended to identify the clinical site for which a catheter was intended to be used so that this application code sets up the system to generate the appropriate signals and treat the echo signals in an appropriate way;
(iv) a code indicative of the dimensions of the probe to enable the image size to be scaled;
(v) a code indicative of the pulse amplitude to be used to control the output power of the ultrasonic pulses if this is critical to the operation of the particular probe;
(vi) a code indicative of whether the particular probe is of the kind already described with reference to FIGS. 12 and 13 or other construction (not shown) which can be regarded as a true phased-array construction.

In fact the ROM can incorporate any information which is characteristic of a particular catheter/probe so that the system can be automatically pre-set by the mere connection of the catheter to the system.

An alternative to the use of a ROM is to use a mechanical lock-and-key type of sensor at the proximal interface i.e. the point at which the catheter is connected to the system as distinct from the distal end of the catheter i.e. that end which carries the probe 2.

FIG. 18

FIG. 18 is a schematic diagram illustrating the manner in which all the information which can be generated by the system is processed to produce displays to assist the medical practitioner.

Essentially the system of the present invention as illustrated in FIG. 1, can be used to present the information to the medical practitioner in one-dimensional, two-dimensional and three-dimensional form.

To illustrate this statement consider the situation where a patient has plaque on the inside of an artery.

As the probe at the "distal" end of the catheter passes in the vicinity of the plaque the echo signals can be used to indicate merely that plaque is there because of the attenuated or modulated reflection which it gives compared with the wall proper of the artery; this is the one-dimensional form referred to and labelled "ID" in FIG. 18.

Additional information concerning the length of the plaque is also available to give the two-dimensional form referred to and labelled "2D" in FIG. 18.

Finally further information concerning the depth of the plaque along its length is available to give the three-dimensional form referred to and labelled "3D" in FIG. 18.

Specifically echo signals from the transducer assembly carried by the probe 2 are sorted at 87 and pre-processed at 88. They are, then fed to a one-dimensional signal generator 89 so that these signals which will give the one-dimensional information referred to earlier are produced. These can be processed at 9D, displayed and manipulated at 92 and used to give a tissue characterisation at 91.

In a similar way echo signals characteristic of the two and three-dimensional visualisations are generated at 93 and 97 respectively, processed at 94 and 98, displayed and manipulated at 96 and 100 and used for tissue characterisation at 95 and 99 respectively.

The tissue characterisation information at 91, 95 and 99 can be fed to an expert system or artificial intelligence system through the interface indicated at 101 whereby an automatic diagnosis of the medical condition is made.

Also represented in FIG. 18 at 102 is the DSA System of FIG. 14, shown at 102, whereby the position of the probe 2 can be fed into the 3D image Generation 97 through a Probe Position Identification step 103. Alternatively the simpler and less informative electronic micrometer means for indicating the position of the probe, and represented at 104, can be fed into 97.

We claim:

1. A method for providing an image of the interior of a human organ or for visualising the flow of blood through it comprising the steps of:
   firing ultrasonic signals either from inside or outside the organ,
   detecting echo signals of said fired ultrasonic signals,
   digitising the echo signals,
   storing the digitised echo signals in a digital computer,
   manipulating the stored digitised echo signals in such a way as to provide an output from the computer which will give a three-dimensional visual representation of the interior of the organ, and
   enabling manipulation of the representation to enable the representation to be viewed from different aspects.

2. A method as claimed in claim 1 in which a three-dimensional representation or model of the human organ is created by means of the following steps:
   (a) obtaining a first approximation to an instantaneous cross-sectional shape or "slice" of the organ by means of the said echo signals;
   (b) Digitising signals corresponding to each "slice" into two-dimensional elements or "pixels";
   (c) Interpolating between points on the cross-section defined by the said echo signals to provide a second approximation to the said instantaneous cross-sectional shape or "slice";
   (d) Integrating a plurality of the bus generated "slices" and interpolating between adjacent "slices" to form a three-dimensional representation of three-dimensional elements or "voxels"; and
   (e) Manipulating the said three dimensional elements or "voxels" to produce a variety of three-dimensional representations of the organ.

3. A method as claimed in claim 1 further comprising the step of superimposing the three-dimensional ultrasonic image on an X-ray image.

4. A method as claimed in claim 1 in which a representation of a flow of blood in the human organ is created by means of the following steps:
   (a) doppler demodulating the stored digitised echo signals to extract a doppler signal therefrom;
   (b) performing a spectral estimation on the doppler signal to calculate the spectral features of the doppler signal;
   (c) performing a velocity estimation on the spectrally estimated signal to calculate fluid flow velocity information;
   (d) performing a three dimensional fluid flow generation to produce a three dimensional flow profile calculation and representation; and
   (e) manipulating the representation produced by step (d) to enable the representation to be viewed from different aspects on a display terminal.

5. Equipment for providing an image of the interior of a human organ within a human body, comprising:
   (a) a catheter for insertion into the human body;
   (b) an ultrasonic transducer assembly mounted on the catheter;
   (c) means for energising the transducer assembly to generate ultrasonic signals;
   (d) means for receiving the resultant ultrasonic echo signals and converting them into digital signals;
   (e1) a digital computer;
   (e2) means for supplying the digital signals from said means for receiving to said digital computer;
   (f) means for manipulating the digital signals to enable a three-dimensional representation of the organ to be created and for enabling that representation to itself be manipulated to enable the representation to be viewed from different aspects and also to enable the structural make-up of tissue to be visually represented; and
   (g) means connected to the computer for visually displaying the three-dimensional representation.

6. Equipment as claimed in claim 5 which includes means generating a spark at or near the distal end of the catheter and detection means, which in use is external of the patient, for detecting the discharge of the spark and thereby producing signals indicative of the position of the spark and hence the distal end of the catheter in relation to the patient.

7. Equipment as claimed in claim 5 which includes means for measuring and indicating the distance which the distal end of the catheter has been inserted into the patient.

8. Equipment as claimed in claim 5 in which the proximal end of the catheter is provided with means for uniquely identifying that catheter, said identification means being adapted to interact with the ultrasonic transducer assembly and processing the resultant echo signals in order to set up the system automatically for use with that particular catheter.

9. A catheter for insertion into a human body and for use with equipment for providing an image of the interior of a human organ within a human body, the equipment including means for receiving resultant ultrasonic echo signals from ultrasonic signals generated by the catheter and for converting the echo signals into digital signals; a digital computer; means for supplying the digital signals from said means for receiving to said digital computer; means for manipulating the digital signals to enable a three-dimensional representation of the organ to be created and for enabling that representation to itself be manipulated to enable the representation to be viewed from different aspects and also to enable the structural make-up of tissue to be visually represented; and means connected to the computer for visually displaying the three-dimensional representation, said catheter comprising:
   (a) a catheter tube;
   (b) a probe carried at one end of the catheter tube;

(c) an ultrasonic transducer arrangement in the form of an annular assembly of transducer elements which encircle the probe at or near one of its ends; and (d) means for electrically connecting the transducer elements to the other end of the catheter tube, which means either incorporates a multiplexing/demultiplexing circuit or comprises a wiring arrangement which has the effect of acting in a multiplexing or demultiplexing way, either the circuit or the arrangement reducing the number of wires which run the length of the catheter tube.

10. A catheter as claimed in claim 9 in which the annular transducer arrangement comprises a plurality of discrete piezo-electric crystal elements arranged in one or more rings coaxially around one end of the catheter tube.

11. A catheter as claimed in claim 10 in which the probe comprises a one-piece plastics member which is shaped to accommodate the transducer arrangement and which has a spigot portion adapted to fit into one end of the catheter tube.

12. A catheter as claimed in claim 10 in which the probe also has mounted on it a further ultrasonic transducer arrangement which is designed to emit ultrasonic signals of a frequency which in use will tend to disintegrate matter which has accumulated on the inside walls of the human organ.

13. A catheter as claimed in claim 9 in which the annular transducer arrangement comprises one or more rings of piezo-electric crystal material arranged coaxially around one end of the catheter tube, each ring being divided into a plurality of areas of each of which is adapted to operate as a separate ultrasonic signal emitting and receiving element.

14. A catheter as claimed in claims 9 which is adapted to accommodate a fibre optic channel for the application of laser angioplasty.

15. A catheter as claimed in claim 9 which incorporates a balloon mounted around and near the probe, the balloon being inflatable by means of air or gas passed down a lumen in the catheter.

16. A catheter as claimed in claim 9 in which the transducer arrangement is rotatably mounted on the probe and means are provided for driving the arrangement to thereby enable the transducer element or elements to rotate about the axis of the probe and thus scan the interior of the organs.

17. A catheter as claimed in claim 9 in which the transducer arrangement consists of a number of pairs of transducer elements, each transducer element of a pair being inclined inwardly towards the other transducer element of the pair so that when in operation the signals generated by the two transducer elements of a pair will focus at a point radially outwardly from the wall of the catheter, each transducer element of a pair being adapted to emit ultrasonic signals at a different frequency from the other transducer element of that same pair.

* * * * *